United States Patent
Tirtowidjojo et al.

(10) Patent No.: US 9,169,177 B2
(45) Date of Patent: Oct. 27, 2015

(54) PROCESS FOR THE PRODUCTION OF TETRACHLOROMETHANE

(71) Applicant: DOW GLOBAL TECHNOLOGIES LLC, Midland, MI (US)

(72) Inventors: Max Markus Tirtowidjojo, Lake Jackson, TX (US); Danny Eugene Randolph, Lake Jackson, TX (US)

(73) Assignee: BLUE CUBE IP LLC, Midland, MI (US)

(*) Notice: Subject to any disclaimer, the term of this patent is extended or adjusted under 35 U.S.C. 154(b) by 0 days.

(21) Appl. No.: 14/366,818

(22) PCT Filed: Dec. 18, 2012

(86) PCT No.: PCT/US2012/070346
§ 371 (c)(1),
(2) Date: Jun. 19, 2014

(87) PCT Pub. No.: WO2013/096311
PCT Pub. Date: Jun. 27, 2013

(65) Prior Publication Data
US 2014/0336425 A1 Nov. 13, 2014

Related U.S. Application Data

(60) Provisional application No. 61/579,105, filed on Dec. 22, 2011.

(51) Int. Cl.
C07C 17/013 (2006.01)
C07C 17/10 (2006.01)

(52) U.S. Cl.
CPC .............. *C07C 17/013* (2013.01); *C07C 17/10* (2013.01)

(58) Field of Classification Search
CPC ............................ C07C 17/10; C07C 17/013
USPC ...................................................... 570/253
See application file for complete search history.

(56) References Cited

U.S. PATENT DOCUMENTS

| | | | |
|---|---|---|---|
| 2,119,484 A | 5/1938 | Levine | |
| 2,179,378 A | 11/1939 | Metzger | |
| 2,207,193 A | 7/1940 | Groll | |
| 2,299,441 A | 10/1942 | Vaughn | |
| 2,302,228 A | 11/1942 | Kharasch | |
| 2,370,342 A | 2/1945 | Zellner | |
| 2,378,859 A | 6/1945 | Martin | |
| 2,435,983 A | 2/1948 | Schmerling | |
| 2,449,286 A | 9/1948 | Fairbairn | |
| 2,588,867 A | 3/1952 | Elton | |
| 2,630,461 A | 3/1953 | Sachsse et al. | |
| 2,688,592 A | 9/1954 | Skeeters | |
| 2,762,611 A | 9/1956 | Monroe | |
| 2,765,359 A | 10/1956 | Pichler et al. | |
| 2,964,579 A | 12/1960 | Weller et al. | |
| 2,973,393 A | 2/1961 | Monroe | |
| 3,000,980 A | 9/1961 | Asadorian | |
| 3,094,567 A | 6/1963 | Eaker | |
| 3,112,988 A | 12/1963 | Coldren et al. | |
| 3,444,263 A | 5/1969 | Fernald | |
| 3,446,859 A | 5/1969 | Weil | |
| 3,502,734 A | 3/1970 | Baird | |
| 3,525,595 A | 8/1970 | Zirngibl Hans et al. | |
| 3,551,512 A | 12/1970 | Loeffler | |
| 3,558,438 A | 1/1971 | Schoenbeck | |
| 3,651,019 A | 3/1972 | Asscher | |
| 3,676,508 A | 7/1972 | Krekeler | |
| 3,819,731 A | 6/1974 | Pitt | |
| 3,823,195 A | 7/1974 | Smith | |
| 3,872,664 A | 3/1975 | Lohmann | |
| 3,914,167 A | 10/1975 | Ivy | |
| 3,920,757 A | 11/1975 | Watson | |
| 3,926,758 A | 12/1975 | Smith | |
| 3,948,858 A | 4/1976 | Wiersum | |
| 3,954,410 A | 5/1976 | Pohl et al. | |
| 4,038,372 A | 7/1977 | Colli | |
| 4,046,656 A * | 9/1977 | Davis et al. | 204/157.99 |
| 4,051,182 A | 9/1977 | Pitt | |
| 4,319,062 A | 3/1982 | Boozalis et al. | |
| 4,513,154 A | 4/1985 | Kurtz | |
| 4,535,194 A | 8/1985 | Woodard | |
| 4,614,572 A | 9/1986 | Holbrook | |
| 4,644,907 A | 2/1987 | Hunter | |

(Continued)

FOREIGN PATENT DOCUMENTS

| | | |
|---|---|---|
| CH | 609022 | 6/1974 |
| CN | 101215220 | 7/2008 |

(Continued)

OTHER PUBLICATIONS

Ochi, et al., "Preparation of Chloropropenes by Photochemical Dehydrochlorination of 1,2-Dichloropropane", Chemical Abstracts, Jul. 17, 1989, p. 574, 111(3).
Bai et al., "Isomerization of Tetrachloropropene to Promote Utilization Ratio of Triallate Raw Materials" Petrochemical Technology & Application, 2007, 25(1).
Boualy et al., "Kharasch Addition of Tetrachloromethane to Alkenes Catalyzed by Metal Acetylacetonates", Catalysis Communications, 2011, pp. 1295-1297, vol. 12.
Chai et al., "Study of Preparation of 1,1,1,3-tetrachloropropane", Zhejiang Huagong Industry, 2010, pp. 1-3, 41(5).
Cristiano et al., Tetraalkylphosphonium Trihalides. Room Temperature Ionic Liquids As Halogenation Reagents, J. Org. Chem., 2009, pp. 9027-9033, vol. 74.
Evstigneev et al., "Initiated Chlorination of Tetrachloropropane", Khim. Prom., 1984, pp. 393-394, 16(7).

(Continued)

*Primary Examiner* — Shailendra Kumar
(74) *Attorney, Agent, or Firm* — Susan Moeller Zerull; KSJLAW, LLC

(57) ABSTRACT

Processes for the production of tetrachloromethane are provided. The present processes involve catalyzing the chlorination of a feedstream comprising partially chlorinated methanes with a free radical initiator. Cost savings are thus provided relative to conventional processes that require the use of high temperatures and/or pressures, and safety concerns are alleviated or eliminated.

13 Claims, 1 Drawing Sheet

(56) References Cited

U.S. PATENT DOCUMENTS

| | | | |
|---|---|---|---|
| 4,650,914 A | 3/1987 | Woodard |
| 4,661,648 A | 4/1987 | Franklin |
| 4,702,809 A | 10/1987 | Mueller |
| 4,714,792 A | 12/1987 | Mueller |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,581,011 B2 | 11/2013 | Tirtowidjojo |
| 8,581,012 B2 | 11/2013 | Tirtowidjojo |
| 8,614,361 B2 | 12/2013 | Suzuki |
| 8,614,363 B2 | 12/2013 | Wilson et al. |
| 8,907,149 B2 | 12/2014 | Tirtowidjojo et al. |
| 8,957,258 B2 * | 2/2015 | Okamoto et al. ............ 568/684 |
| 9,067,855 B2 | 6/2015 | Grandbois et al. |
| 2001/0018962 A1 | 9/2001 | Joshi et al. |
| 2002/0110711 A1 | 8/2002 | Boneberg et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0088547 A1* | 4/2009 | Schamschurin et al. ........ 528/14 |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose et al. |
| 2014/0081055 A1 | 3/2014 | Tirtowidjojo |
| 2014/0179962 A1 | 6/2014 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |

(56) References Cited

FOREIGN PATENT DOCUMENTS

| | | |
|---|---|---|
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2013078035 | 5/2013 |
| WO | 2013082410 | 6/2013 |

OTHER PUBLICATIONS

Fields et al., "Thermal Isomerization of 1,1-dichlorocyclopropanes", Chemical Communications, Jan. 1, 1967, 1081, No. 21.

Galitzenstein et al., "The Dehydrochlorination of Propylene Dichloride", Journal of the Society of Chemical Industry, 1950, pp. 298-304, vol. 69.

Gault et al., "Chlorination of Chloroform" Comptes Rendus Des Seances De L'Academie des Sciences, 1924, pp. 467-469, vol. 179.

Gerding et al, "Raman Spectra of aliphatic chlorine compounds: chloroethenes an chloropropenes", Recueil Jan. 1, 1955, pp. 957-975, vol. 74.

Hatch et al., "Allylic Chlorides. XV. Preparation and Properties of the 1,2,3Trichloropropenes". JACS, Jan. 5, 1952, pp. 123-126, vol. 74.

Hatch et al., "Allylic Chlorides. XVIII. Preparation and Properties of 1,1,3-tricholoro-2-fluoro-1-propene and 1,1,2,3-tetrachloro-1-propene". JACS, Jul. 5, 1952, pp. 3328-3330, 74(13).

Herzfelder, "Substitution in the Aliphatic Series", Berichte Der Deutschen Chemischen Gesellschaft, May-Aug. 1893, pp. 1257-1261, 26(2).

Ivanov et al., "Metal phthalocyanine-Catalyzed Addition of polychlorine-Containing Organic Compounds to C=C Bonds," Russian Chemical Bulletin, International Edition, Nov. 2009, pp. 2393-2396, 58(11).

Kang et al., Kinetics of Synthesis of 1,1,1,3,3-pentachlorobutane Catalyzed by Fe—FeCl3, Chemical Research and Application, Jun. 2011, pp. 657-660, 23(6).

Kharasch et al., "Chlorinations with Sulfuryl Chloride.I. The Peroxide-Catalyzed Chlorination of Hydrocarbons", JACS, 1939, pp. 2142-2150, vol. 61.

Khusnutdinov et al., CCl4 Attachment to Olefins Catalyzed by Chromium and Ruthenium Complexes. Impact of Water as a Nucleophilic Admixture, Oil Chemistry, 2009, pp. 349-356, vol. 4.

Kruper et al., "Synthesis of alpha-Halocinnamate Esters via Solvolytic Rearrangement of Trichloroallyl Alcohols", , J Org Chem, 1991, pp. 3323-3329, vol. 56.

Leitch, "Organic Deuterium Compounds: V. The chlorination of propyne and propyne D-4", Canadian Journal of Chemistry, Apr. 1, 1953, pp. 385-386, 30(4).

Levanova et al.. "Thermocatalytic Reactions of Bromochloropropanes", Russian Journal of Physical Chemistry, Jan. 1, 1983, pp. 1142-1146, vol. 57.

Liu et al., "Progress in Synthesis of 1,1,1,3-tetrachloropropane", Guangzhou Chemicals, 2011, pp. 41-42, 39(5).

McBee et al., Utilization of Polychloropropanes and Hexachloroethane, Industrial and Engineering Chemistry, Feb. 1, 1941, pp. 176-181, 33(2).

Mouneyrat, "Effect of Chlorine on Propyl Chloride in the Presence of Anhydrous Aluminum Chloride" Bulletin de la Societe chimique de france, Societe francaise de chimie, vol. 3, No. 21, Jan. 1, 1899.

Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.

Nair et al., "Atom transfer radical addition (ATRA) of carbon tetra-chloride and chlorinated esters to various olefins catalyzed by CP/Ru(PPh3)(PR3)Cl complexes", Inorganica Chimica Acta, 380 2012, 96-103.

Nguyen et al., Condensation de chloroforme avec des olefins fluorees en milieu basique, Journal of Fluorine Chemistry, vol. 55, No. 3, Dec. 1, 1991, pp. 241-248.

Nikishin et al, "Reactions of Methanol and Ethanol with Tetrachloroethylene," N.D. Zelinskii Institute of Organic Chemistry, Academy of Sciences of the USSR, 2115-2119. Translated from Izvestiya Akademii Nauk SSSR, Seriya Khimicheskaya 1966, 12, 2188-2192.

Pozdnev et al., "Chlorination of chloroform and the conversion of methylene chloride manufacture still residues", Khim., Khim. Tekhnol. (1970) 70-4.

Rotshtein et al., "Isomer Distribution on Chlorination of Chloropropanes", Z. Organicheskoi Khimii, 2(9), pp. 1539-1542 (1966).

Semenov, "Selectivity of Photochemical Chlorination of Chloromethane in the Liquid Phase", Prikladnei Khimii, vol. 58, No. 4, pp. 840-845 (1985).

Shelton et al., "Addition of Halogens and Halogen Compounds to Allylic Chlorides. I. Addition of Hydrogen Halides," Journal of Organic Chemistry, 23, pp. 1876-1880 (1958).

Skell, et al., "Reactions of BrCl with alkyl radicals", Tetrahedron letters, vol. 27, No. 43, pp. 5181-5184, 1986.

Skell et al., "Selectivities of pi and sigma succinimidyl radicals in substitution and addition reactions, Response to Walling, Wl-Taliawi and Zhao", JACS, vol. 105, No. 15, Jul. 1, 1983, p. 5125-5131.

Tanuma et al., "Partially Fluorinated Metal Oxide Catalysts for a Friedel-Crafts-type Reaction of Dichlorofluoromethane with Tetrafluoroethylene", Catal. Lett. (2010) 136:77-82.

Tobey et al., "Pentachlorocyclopropane 1" Journal of the American Chemical Society, vol. 88, No. 11, Jun. 1, 1996 pp. 2478-2481.

Urry et al., "Free Radical Reactions of Diazomethane with Reactive Bromopolychloroalkane", JACS, vol. 86, No. 9, May 5, 1964, p. 1815-1819.

Wang Chin-Hsien, Elimination Reactions of polyhaloprppanes under emulsion catalytic conditions to give Halopropenes, Synthesis, Teorg Thieme Verlag, Stuttgart, De, vol. 1982, No. 6, Jan. 1, 1982, pp. 494-496.

Zhao et al., Zhejiang Chemical Industry, vol. 41, No. 6, p. 8-10 (2010).

Zheng et al., "Preparation of the low GWP alternative 1,3,3,3-tetrafluoropropene", Zhejiang Huagong (2010) 41(3), 5-7.

Stevens, "Some New Cyclopropanes with a Note on the Exterior Valence Angles of Cyclopropane", JACS, Vo. 68, No. 4, 1945, 620-622.

Levanova, et al., "Cholorination of Chloroolefins C3-C4", Doklady Chemistry, vol. 386, No. 4, 2002, 496-498.

Michigan Technological Univ., "Free-Radical Chlorination with Sulfuryl Chloride", Nov. 15, 2001, 1-7.

\* cited by examiner

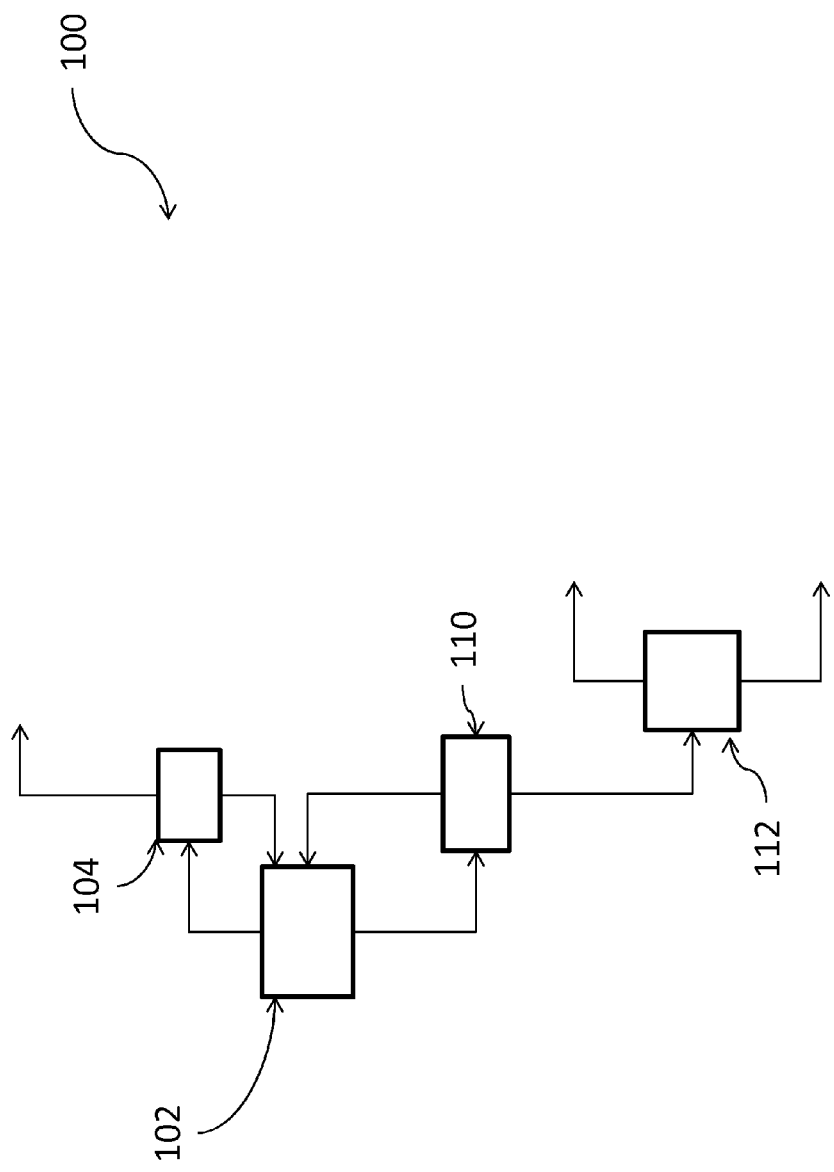

PROCESS FOR THE PRODUCTION OF TETRACHLOROMETHANE

This application is a 371 of PCT/US2012/070346, filed Dec. 18, 2012, which claims benefit of 61/579,105, filed Dec. 22, 2011.

FIELD

The present invention relates to processes for the production of tetrachloromethane.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form their much lower GWP. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene, may typically be produced utilizing feedstocks of chlorocarbons, and in particular, chlorinated propanes and/or propenes, which may also find use as feedstocks for the manufacture of polyurethane blowing agents, biocides and polymers.

Unfortunately, many chlorinated propenes may have limited commercial availability, and/or may only be available at prohibitively high cost. This may be due at least in part to the fact that conventional processes for their manufacture may require the use of raw materials and/or starting materials that are prohibitively expensive, or otherwise too limited in the throughputs that can be achieved, to be economically produced by manufacturers on the large scale required to be useful as feedstocks.

For example, some conventional processes may require highly chlorinated propanes or propenes as starting materials that are, in turn, prepared from raw materials that are not generally readily available. Such raw materials may be produced in limited quantities as by-products of other processes, or, may be produced by processes that may be less than optimal in terms of selectivity and/or yield, process operating and/or capital cost, safety, and/or environmental acceptability.

It would thus be desirable to provide improved processes for the production of raw materials useful in the synthesis of chlorocarbon precursors that in turn, are useful as feedstocks in the synthesis of refrigerants and other commercial products. More particularly, such processes would provide an improvement over the current state of the art if they provided a commercially useful yield and/or selectivity, were operable under lower intensity, and thus safer, conditions.

BRIEF DESCRIPTION

The present invention provides processes for the production of tetrachloromethane. Advantageously, the processes make use of partially chlorinated methanes as starting material, and, catalyze the chlorination of the same with a free radical catalyst. As a result, lower intensity process conditions than conventional processes for the production of tetrachloromethane, utilizing methane as a starting material, can be used. Although lower temperatures and pressures are used, and cost savings thus provided, chloroform and tetrachloromethane are produced in higher yields than provided by conventional processes. By maintaining conversion rates of less than 90%, greater reaction selectivity to tetrachloromethane may be seen, along with production of anhydrous HCl as a reaction byproduct. Recycling of reactants can increase the reaction yield and overall conversion, and provide even further cost savings.

In one aspect, the present invention provides a process for the production of tetrachloromethane. The process comprises catalyzing the chlorination of a feed stream comprising partially chlorinated methanes with a free radical catalyst. The process may be conducted in the liquid phase, in the presence of a solvent. In some embodiments, the solvent may be tetrachloromethane produced by the process. In some embodiments, the feedstream does not comprise methane, and in such embodiments, or other embodiments, the feedstream may comprise chloroform, either alone or in combination with methyl chloride and/or methylene chloride. The free radical catalyst may comprise UV-light, azobisisobutyronitrile, 1,1'-azobis(cyclohexanecarbonitrile), di-tert-butyl peroxide, benzoyl peroxide, methyl ethyl ketone peroxide, acetone peroxide or combinations of any number of these. The temperature of the process may be less than 100° C., and the pressure is desirably less than 100 psig. In some embodiments, anhydrous HCl may be recovered from the process.

The advantages provided by the present processes may be carried forward by utilizing the tetrachloromethane to produce further downstream products, such as, e.g., 1,1,1,2,3-pentachloroproprane and/or 1,1,2,3-tetrachloropropene.

DESCRIPTION OF THE FIGURES

FIG. 1 shows a schematic representation of a process for the production of tetrachloromethane according to one embodiment.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Further, "M1" may be used as an abbreviation for chloromethane or methyl chloride ($CH_3Cl$), "M2" may be used as an abbreviation for dichloromethane or methylene chloride ($CH_2Cl_2$), "M3" may be used as an abbreviation for trichloromethane or chloroform ($CHCl_3$) and "M4" may be used as an abbreviation for tetrachloromethane or carbon tetrachloride ($CCl_4$).

The present invention provides efficient processes for the production of tetrachloromethane. Tetrachloromethane is an important raw material desirably utilized in the production of, e.g., 1,1,1,2,3-pentachloropropane and/or 1,1,2,3-tetrachloropropene. Prior to the present invention, tetrachloromethane was produced mainly as a byproduct from processes for the production of perchloroethylene, and in quantities insufficient for use as a feedstock in many processes. Although processes for the direct production of tetrachloromethane are known, these conventional processes may typically require the use of high intensity process conditions, e.g., high temperatures and pressures, and yet provided poor yields and selectivities to tetrachloromethane. Furthermore, processes employing such conditions are known by the art to be volatile, and often, explosive. And, the use of high intensity process conditions adds cost to a process, not only in the form of utility costs, but of the specialized equipment that may be necessary to achieve and/or house such conditions.

The present processes make use of a feedstream comprising partially chlorinated methanes. In some embodiments, the feedstream may comprise chloroform, either alone or in combination with methyl chloride and/or methylene chloride. In these, or other, embodiments, the feedstream may be devoid of methane. The absence of methane from the feedstream is advantageous because methane is not very soluble in tetrachloromethane, and so, in its presence, high pressures would be required to keep methane in solution in the reaction mixture. Since the present processes do not make use of methane as a reactant, lower pressures may be used, and less capital and energy costs incurred.

The chlorination of the feedstream is desirably catalyzed with one or more free radical initiators. The use of one or more free radical initiators not only provides the reaction with an acceptable rate, but can also increase the yield of tetrachloromethane, as well as the selectivity to chloromethane, particularly when conversions of the feedstream are limited to less than 90%, or less than 80%, or less than 70% or even to 60%. More specifically, at a feedstream conversion of 60%, chloroform and tetrachloromethane may be produced at ratios of 4:1, or 1:1 or even 1:2, with very little production of methyl chloride or methylene chloride.

Many free radical initiators are known, and any of these may be used in the present processes. Examples of suitable free radical initiators include, but are not limited to, compounds comprising one or more azo-groups (R—N=N—R') such as azobisisobutyronitrile (AIBN) or 1,1'-azobis(cyclohexanecarbonitrile) (ABCN) and organic peroxides such as di-tert-butyl peroxide, benzoyl peroxide, methyl ethyl ketone peroxide, and acetone peroxide. Combinations of any number of these may also be utilized. In some embodiments, the use of AIBN may be preferred, either alone or in combination with UV or visible light or heat.

The desired free radical initiator(s) can be provided either in bulk or in connection with a substrate, such as activated carbon, graphite, silica, alumina, zeolites, fluorinated graphite and fluorinated alumina.

The amount of the desired free radical initiator will depend upon the particular initiator chosen as well as the other reaction conditions. Generally speaking, enough of the initiator should be utilized to provide some improvement to reaction process conditions (e.g., a reduction in required temperature) or realized products, but yet not be more than will provide any additional benefit, if only for reasons of economic practicality.

For purposes of illustration only, useful concentrations of free radical initiators will range from 0.0001% to 10% by weight each with respect to, or from 0.001% to 1%, or preferably from 0.01% to 0.1 wt %, inclusive of all subranges therebetween.

Due at least in part to the use of at least one free radical initiator, as well as perhaps, at least in some embodiments, the exclusion of methane from the feedstream, the present processes may be carried out at lower intensity conditions, e.g., lower pressures and/or temperatures, than conventional processes. More particularly, the present processes may desirably be carried out at pressures of less than or equal to 140 psig, or less than or equal to 120 psig, or even less than or equal to 100 psig. Further, temperatures of less than or equal to 150° C., or less than or equal to 120° C., or less than or equal to 100° C., are appropriate. In some embodiments, unreacted reactants may be recycled, or other solvents may be utilized, to assist with heat management within the reactor. The process may be conducted in the liquid phase, in the presence of a solvent. In some embodiments, tetrachloromethane produced by the process may act as a solvent.

The use of both a low temperature and a low pressure is also contemplated, but not required, and in embodiments wherein the use of both is desired, any combination of any temperature of less than or equal to 120° C. and any pressure less than or equal to 100 psig may be utilized. For example, if the pressure is desirably less than or equal to 140 psig, the temperature may be ambient, or less than or equal to 120° C., or less than or equal to 100° C. Similarly, if the pressure is desirably less than or equal to 120 psig, the temperature may be ambient, or less than or equal to 140° C., or less than or equal to 120° C., or less than or equal to 100° C., and so on.

In some embodiments, the present processes are desirably conducted in the liquid phase. Liquid phase processes for the production of tetrachloromethane may provide advantages as compared to conventional methods for producing tetrachloromethane using gas-phase reactions at least because the production utility cost is lower for liquid phase processes, where evaporation of reactants is not required. In addition, the lower reaction temperatures used in the present liquid phase processes tend to result in lower fouling rates than the higher temperatures used in connection with gas phase processes. Higher fouling rates, in turn, tend to limit reactor lifetime and can lead to undesirable byproduct formation.

The chlorination steps of the process may be carried out using any chlorination agent, and several of these are known in the art. Exemplary chlorination agents include, but are not limited to chlorine, and/or sulfuryl chloride ($SO_2Cl_2$). If sulfuryl chloride is used, the by-product $SO_2$ may be catalytically recombined with $Cl_2$ to regenerate sulfuryl chloride that may then be recycled to the process.

The present processes may be conducted in any suitable reactor, and are desirably conducted using reactors that are capable of continuous operation. In some embodiments, the processes may advantageously be conducted in a continuous stirred tank reactor. Stirring of the reaction mixture may lead to enhanced reaction rate, and thus can be utilized in some embodiments.

Economics of the process, e.g., as witnessed by yield and/or selectivity, may be enhanced by recycling of unreacted reactants to the reactor. Such recycling may also assist in heat regulation of the process. Economics of the process may further be enhanced by allowing for the recovery of one or more usable byproducts, such as hydrogen chloride. And so, in some embodiments, provisions are made for the same. For example, hydrogen chloride may be recovered from the process via implementation of a distillation column, wherein the feedstream to the same, and from which hydrogen chloride is desirably recovered, is condensed at a temperature of from −40° C. to 0° C. prior to introduction to the distillation column.

In additional embodiments, one or more reaction conditions of the process may be optimized, in order to provide even further advantages, i.e., improvements in selectivity, conversion or production of reaction by-products. In certain embodiments, multiple reaction conditions are optimized and even further improvements in selectivity, conversion and production of reaction by-products produced can be seen.

Reaction conditions of the process that may be optimized include any reaction condition conveniently adjusted, e.g., that may be adjusted via utilization of equipment and/or materials already present in the manufacturing footprint, or that may be obtained at low resource cost. Examples of such conditions may include, but are not limited to, adjustments to flow rates, molar ratios of reactants, etc.

That being said, the particular conditions employed at each step described herein are not critical, and are readily determined by those of ordinary skill in the art. What is important is that a feedstream comprising partially chlorinated methanes is catalyzed with a free radical catalyst to provide tetrachloromethane. The feedstream may comprise either or both chloroform and methylene chloride, and may further comprise methyl chloride and desirably does not comprise methane. It is also advantageous that anhydrous HCl is produced. Further advantages may be provided in those embodiments in which the process is conducted in the liquid phase. Those of ordinary skill in the art will readily be able to determine suitable equipment for each step, as well as the particular conditions at which the steps are desirably performed.

A schematic illustration of such a process is shown in FIG. 1. As shown in FIG. 1, in process 100, a feedstream comprising a mixture of chloromethane and methylene chloride is chlorinated in the liquid phase in reactor 102 to produce chloroform and tetrachloromethane. The overhead stream from reactor 102, comprising excess chlorine, HCl, methyl chloride and methylene chloride, is fed to a separation column 104 where HCl is purified in the overhead stream. The bottom stream of separation column 104 comprising unreacted chlorine, methyl chloride, and methylene chloride is recycled back to reactor 102. The organic liquid product of reactor 102, comprising methyl chloride, methylene chloride, chloroform and tetrachloromethane, is sent to a separation column 110, which provides an overhead stream comprising methyl chloride, methylene chloride and chloroform that is recycled back to reactor 102. The bottom stream of separation column 110 comprising tetrachloromethane and heavier byproducts is provided to separation column 112. In column 112, tetrachloromethane is purified and provided as an overhead product stream, and the heavier byproducts are disposed of through a bottom stream.

The tetrachloromethane produced by the present process may typically be processed to provide further downstream products including hydrofluoroolefins, such as, for example, 1,1,1,2,3-pentachloroproprane and/or 1,1,2,3-tetrachloropropene. Since the present invention provides an improved process for the production of tetrachloromethane, it is contemplated that the improvements provided will carry forward to provide improvements to these downstream processes and/or products. Improved processes for the production of tetra- and penta-chloropropanes and/or chloropropenes are thus also provided herein.

The conversion of tetrachloromethane to tetra- and penta-chloropropanes and/or chloropropenes may broadly comprise the catalyzed reaction of tetrachloromethane and ethylene. A more specific example might involve a process wherein a feedstream of tetrachloromethane is reacted with ethylene in the presence of less than 2 mole % of one or more catalysts comprising iron, such as FeCl3, and optionally, from 0.1 to 5 mole % a phosphours containing promoter. The reaction is generally carried out at temperatures of from 50° C. to 150° C. and pressure of from 1 atm to 14 atm. At such conditions, conversions of tetrachloromethane of from 80% to 100% are expected, with the main product being 1,1,1,2,3-pentachloropropane.

Some embodiments of the invention will now be described in the following Examples.

Example 1

Conversion of Methylene Chloride to Chloroform and Tetrachloromethane

Methylene chloride (M2) is reacted with chlorine in the liquid phase at 82° C. and 70 psig in the presence of a 40 watt UV black light in a 1 inch ID tube reactor jacketed with circulating water from a 15° C. temperature-regulated water bath at ambient pressure. The organic phase is analyzed on a Varian 6000 gas chromatograph equipped with a 30 meter DB-5 fused-silica capillary column. Using 69-70 minute residence time and a methylene chloride/chlorine molar feed ratio of 1.32, liquid product analysis shows 22.72 wt %, 53.3 wt %, and 24 wt % of the methylene chloride, chloroform, and tetrachloromethane, respectively. In other words, a 3/1 chloroform/tetrachloromethane molar product ratio is obtained at 66% methylene chloride conversion.

Example 2

Conversion of Methyl Chloride and Methylene Chloride to Chloroform and Tetrachloromethane Methyl chloride and methylene chloride, at a molar ratio of 1/4, are reacted with chlorine in the liquid phase in the presence of 100 ppm of AIBN at 70 psig and 84° C. in a ½ inch ID and 18 inch long tube. At flow rates of 1, 4, and 2.5 grmole/hr of methyl chloride, methylene chloride and chlorine, respectively, methyl chloride and methylene chloride conversions of 61.4 and 27.5%, respectively, are obtained. The product mixture comprises 4.1 wt. % methyl chloride, 48.4 wt. % methylene chloride, 38.0 wt. % chloroform, and 9.5 wt. % tetrachloromethane. The ratio of chloroform to tetrachloromethane is found to be 5.2.

Example 3

Chlorination of Chloroform to Tetrachloromethane

Forty five to 55 gallons of liquid chloroform was chlorinated at a temperature of from 35° C. to 40° C. using 400 watt H1 mercury vapor lamp with a wavelength of from 300 to 500 millimicrons. The reaction is conducted in a 30 inch ID nickel tank equipped with triangular chlorine bubbler and three-light well. The percent tetrachloromethane in the liquid product is determined using specific gravity. After adding 300 lbs of $Cl_2$, 95 mole % of tetrachloromethane is obtained in the product mixture.

The invention claimed is:

1. A process for the production of tetrachloromethane comprising catalyzing the chlorination of a feedstream comprising methylene chloride and/or methyl chloride, and not comprising chloroform or methane, with a free radical initiator to provide a product stream comprising chloroform and tetrachloromethane at a ratio of from 4:1 to 1:2.

2. The process of claim 1, wherein the reaction is conducted in the liquid phase.

3. The process of claim 2, wherein the reaction is conducted in a solvent.

4. The process of claim 3, wherein the tetrachloromethane produced acts as a solvent.

5. The process of claim 1, wherein the free radical initiator comprises UV-light, azobisisobutyronitrile, 1,1'-azobis(cyclohexanecarbonitrile), di-tert-butyl peroxide, benzoyl peroxide, methyl ethyl ketone peroxide, acetone peroxide or combinations of any number of these.

6. The process of claim 5, wherein the free radical initiator comprises azobisisobutyronitrile.

7. The process of claim 6, wherein the free radical initiator comprises azobisisobutyronitrile and UV-light.

8. The process of claim 2, wherein the process is carried out a temperature of less than 150° C.

9. The process of claim 1, wherein the process is carried out at a pressure of less than 140 psig.

10. The process of claim 1, wherein HCl is generated as a byproduct and recovered as anhydrous HCl.

11. The process of claim 1, wherein the source of chlorine atoms comprises chlorine, sulfuryl chloride, or a combination of these.

12. The process of claim 1, further comprising recycling unreacted methylene chloride and/or methyl chloride to the chlorination reactor.

13. The process of claim 12, wherein the recycle stream further comprises chloroform.

* * * * *